United States Patent
Herfert et al.

(10) Patent No.: US 7,329,701 B2
(45) Date of Patent: *Feb. 12, 2008

(54) SUPERABSORBENT POLYMERS AND METHOD OF MANUFACTURING THE SAME

(75) Inventors: Norbert Herfert, Charlotte, NC (US); Michael M. Azad, Charlotte, NC (US); Michael A. Mitchell, Waxhaw, NC (US); Guy Thomas Woodrum, Suffolk, VA (US); William G.-J. Chiang, Yorktown, VA (US); Patricia D. Brown, Charlotte, NC (US); James C. Robinson, Chesapeake, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 233 days.

This patent is subject to a terminal disclaimer.

(21) Appl. No.: 10/522,937

(22) PCT Filed: Jul. 24, 2003

(86) PCT No.: PCT/EP03/08087

§ 371 (c)(1),
(2), (4) Date: Jan. 31, 2005

(87) PCT Pub. No.: WO2004/018005

PCT Pub. Date: Mar. 4, 2004

(65) Prior Publication Data

US 2005/0239942 A1    Oct. 27, 2005

Related U.S. Application Data

(60) Provisional application No. 60/405,477, filed on Aug. 23, 2002.

(51) Int. Cl.
C08K 3/34 (2006.01)

(52) U.S. Cl. ............... 524/445; 524/556; 524/832; 525/330.2

(58) Field of Classification Search ......... 524/445, 524/556, 832; 525/330.2
See application file for complete search history.

(56) References Cited

U.S. PATENT DOCUMENTS

| | | | |
|---|---|---|---|
| 4,286,082 A | 8/1981 | Tsubakimoto et al. | |
| 4,351,754 A | 9/1982 | Dupre | |
| 4,500,670 A * | 2/1985 | McKinley et al. | 524/445 |
| 4,535,098 A | 8/1985 | Evani et al. | |
| 4,654,039 A | 3/1987 | Brandt et al. | |
| 4,666,983 A | 5/1987 | Tsubakimoto et al. | |
| 4,734,478 A | 3/1988 | Tsubakimoto et al. | |
| 4,735,987 A | 4/1988 | Morita et al. | |
| 4,795,482 A | 1/1989 | Gioffre et al. | |
| 4,914,066 A | 4/1990 | Woodrum | |
| 4,990,338 A | 2/1991 | Blank et al. | |
| 5,035,892 A | 7/1991 | Blank et al. | |
| 5,140,076 A | 8/1992 | Hatsuda et al. | |
| 5,218,011 A | 6/1993 | Freeman | |
| 5,409,771 A | 4/1995 | Dahmen et al. | |
| 5,419,956 A | 5/1995 | Roe | |
| 5,559,335 A | 9/1996 | Zeng et al. | |
| 5,669,894 A | 9/1997 | Goldman et al. | |
| 5,733,576 A | 3/1998 | Chmelir | |
| 5,856,410 A * | 1/1999 | Carrico et al. | 525/362 |
| 5,869,033 A * | 2/1999 | Schulz | 424/78.02 |
| 6,056,854 A | 5/2000 | Woodrum | |
| 6,124,391 A | 9/2000 | Sun et al. | |
| 6,565,768 B1 | 5/2003 | Dentler et al. | |
| 6,596,921 B2 * | 7/2003 | Beihoffer et al. | 604/372 |
| 6,602,950 B1 | 8/2003 | Dentler et al. | |
| 6,777,480 B2 | 8/2004 | Payzant et al. | |
| 6,793,930 B2 | 9/2004 | Gatto et al. | |
| 6,849,665 B2 | 2/2005 | Frenz et al. | |
| 6,875,832 B2 | 4/2005 | White et al. | |
| 2002/0006886 A1 | 1/2002 | Beerse et al. | |
| 2002/0017453 A1 | 2/2002 | Iguchi | |
| 2005/0245393 A1* | 11/2005 | Herfert et al. | 502/402 |

FOREIGN PATENT DOCUMENTS

| | | |
|---|---|---|
| CA | 2381930 | 2/2002 |
| EP | 341951 | 11/1989 |
| EP | 799861 | 10/1997 |
| EP | 1506788 | 2/2005 |
| GB | 2082614 | 3/1982 |
| JP | 56 133028 | 10/1981 |
| JP | 61-017542 | 1/1986 |
| WO | WO 87/00848 | 2/1987 |
| WO | WO 91/12029 | 8/1991 |
| WO | WO 91/12031 | 8/1991 |
| WO | WO 98/52979 | 11/1998 |
| WO | WO 99/55767 | 11/1999 |
| WO | WO 99/64515 | 12/1999 |
| WO | WO 00/72958 | 12/2000 |
| WO | WO 00/73596 | 12/2000 |
| WO | WO 0072958 A1 * | 12/2000 |
| WO | WO 01/13965 | 3/2001 |
| WO | WO 01/32117 | 5/2001 |
| WO | WO 01/68156 | 9/2001 |

* cited by examiner

Primary Examiner—David W. Wu
Assistant Examiner—Satya Sastri
(74) Attorney, Agent, or Firm—Marshall, Gerstein & Borun LLP

(57) ABSTRACT

Superabsorbent polymer (SAP) particels containing a clay are disclosed. The clay is added to an SAP hydrogel prior to SAP neutralization to provide particles having improved fluid acquisition rates and an improved permeability of a fluid through the swollen SAP-clay particles. Diaper cores and absorbent articles containing the SAP-clay particles also are disclosed.

29 Claims, No Drawings

SUPERABSORBENT POLYMERS AND METHOD OF MANUFACTURING THE SAME

CROSS-REFERENCE TO RELATED APPLICATIONS

This is the U.S. national phase application of International Application No. PCT/EP2003/008087, filed Jul. 24, 2003, which claims the benefit of U.S. provisional patent application Ser. No. 60/405,477, filed Aug. 23, 2002.

FIELD OF THE INVENTION

The present invention relates to superabsorbent polymers (SAPs) and to a method of manufacturing SAPs. More particularly, the present invention relates to the incorporation of a clay into an SAP hydrogel prior to neutralizing and drying the SAP hydrogel. The resulting clay containing SAP particles exhibit excellent fluid absorption and retention properties, especially with respect to fluid acquisition rates by a diaper core containing the SAP-clay particles.

BACKGROUND OF THE INVENTION

Water-absorbing resins are widely used in sanitary and hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, crosslinked and partially neutralized copolymers of isobutylene and maleic anhydride, saponification products of vinyl acetate-acrylic acid copolymer, sulfonated polystyrenes, hydrolyzed polyacrylamides, polyvinyl alcohols, polyethylene oxides, polyvinylpyrrolidones, and polyacrylonitriles.

These polymers, and others, are known in the art by various names, such as superabsorbent polymers, hydrogels, hydrocolloids, and water-absorbent hydrophilic polymers, for example. As used herein, the term "SAP" refers to a superabsorbent polymer, and collectively refers to such water-absorbing materials. As used herein, the term "SAP particles" refers to superabsorbent polymer particles in the dry state, more specifically, particles containing from no water up to an amount of water less than the weight of the particles, and typically less than about 5%, by weight, water. The terms "SAP gel," "SAP hydrogel," or "hydrogel" refer to a superabsorbent polymer in the hydrated state, more specifically, particles that have absorbed at least their weight in water, and typically several times their weight in water.

SAPs are lightly crosslinked hydrophilic polymers, and are discussed generally in Goldman et al. U.S. Pat. Nos. 5,669,894 and 5,59,335, each incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

An SAP typically is neutralized at least about 25 mole percent, preferably at least about 50 mole percent, and usually about 70 to 80 mole percent, to achieve optimum absorbency. Neutralization can be achieved by neutralizing the acrylic acid monomer before polymerization of the monomer, or the polymer can be neutralized after the polymerization reaction is substantially complete. After polymerization and internal crosslinking of the monomer, followed by partial neutralization, e.g., 50-100 mole percent neutralization, preferably 70 to 80 mole percent neutralization, the polymer is subdivided, e.g., shredded or chopped, for more efficient drying, then dried and milled to a desired particle size. The polymer preferably then is surface crosslinked and again dried to form the final product.

Many improvements have been made in the performance and properties of SAPs, such as in gel strength and reabsorbing capacity. However, investigators are continually searching for additional improvements, for example, in SAP permeability and fluid acquisition rates, such that the amount of cellulosic fiber in a diaper core can be reduced. Reducing the amount of fiber permits the manufacture of a thinner diaper, which is extremely important in adult incontinence articles.

Clays and other mineral products have been added to SAPs in an attempt to improve SAP performance. For example, the addition of finely divided amorphous silica, such as AEROSIL®, available from Degussa, DE, or CAB-O-SIL®, available from Cabot Corporation, or a bentonite onto the surface of SAP powders or granules is known. U.S. Pat. Nos. 5,140,076 and 4,734,478 disclose the addtion of silica during surface crosslinking of dry SAP powders. U.S. Pat. No. 4,286,082 discloses mixtures of silica and an SAP for use in hygiene articles.

JP 65 133 028A and JP 61 017 542B disclose mixtures of hydrophobic silicas and absorbent polymers. EP 0 341 951, U.S. Pat. No. 4,990,338, and U.S. Pat. No. 5,035,892 disclose the use of silica in the production of antimicrobial absorbent polymers. U.S. Pat. No. 4,535,098 and EP 0 227 666 disclose the addition of silica-based colloidal substances to enhance the gel strength of SAPs.

Generally, in mixtures of dry SAP particles with a silica powder, the silica adheres to the SAP particle surfaces and alters the surface properties of the SAP particles, but not their intrinsic absorption properties. For example, the silica powder is hydrophilic or hydrophobic, which primarily influences the rate at which a fluid is absorbed by the SAP particles.

WO 99/64515 discloses the preparation of SAPs by polymerizing olefinically unsaturated carboxylic acids and adding a silicate before, during, and after polymerization. The swollen polymer particles have improved mechanical stability and enhanced permeability. However, because the silicate framework lacks a charge, no osmotic pressure can be generated. This neutral silicate framework does not contribute to the osmotic swell pressure of the hydrogel, and fluid absorbency is adversely effected.

WO 99/55767 discloses ionically crosslinked SAPs obtained by polymerizing carboxyl-containing monomers and adding aluminate ions before, during, and after polymerization. The presence of ionic crosslinked sites provides improved gel stability under mechanical load. However, the salt stability of these hydrogels is inadequate, and a premature collapse of the network structure occurs at a high salt content.

Other patents and applications disclosing SAP particles and a clay include GB 2,082,614 disclosing a dry, solid, water-swellable absorbent composition prepared by blending dry SAP particles and 1% to 75%, by weight of the blend, of an extender material selected from uncrosslinked cellulose derivatives, starch, certain clays and minerals, and mixtures thereof.

U.S. Pat. No. 4,500,670 discloses water-absorbent compositions containing a water-swellable SAP and an inorganic powder, preferably a clay. The compositions are prepared by physically blending the inorganic powder and SAP particles after the SAP is polymerized and crosslinked.

U.S. Pat. No. 4,735,987 discloses polymerization of a partially neutralized acrylic acid via an inverse suspension polymerization process, with the simultaneous addition of a crosslinker and an inorganic material, e.g., a clay, to the polymer bead suspension, followed by azeotropic dehydration. Crosslinking occurs in the presence of the clay during the dehydration step. The resulting product has a high volume expansion after swelling in saline solution.

U.S. Pat. No. 4,914,066 discloses pellets containing 0.5 to 15 wt. % SAP and 85 to 99.5 wt. % bentonite clay, prepared by mixing the SAP and bentonite in the presence of water, then compressing and extruding the blend through an orifice to form the pellets, followed by drying.

WO 91/12029 and WO 91/12031 disclose compositions containing an SAP combined with odor-controlling agents, preferred zeolites, by means of a binder. The SAP particles are coated with the zeolite in presence of a binder in a fluidized bed coating apparatus, or are admixed with dry SAP particles and water, and the mixture is dried by heating.

U.S. Pat. No. 5,419,956 discloses mixtures of SAP fines with an inorganic powder, like silica or clay.

U.S. Pat. No. 5,733,576 discloses a process of producing absorbing agents containing (a) a water-swellable, synthetic polymer or copolymer, and (b) a natural or synthetic polymeric compound which at normal temperature is a pourable powder and is partially soluble or insoluble in water. The absorbing agents can contain clay as a neutral filling agent.

EP 0 799 861 discloses a particulate deodorant composition containing an SAP and powdery zeolite dispersed within the SAP resin particles. The composition is prepared by kneading a water-absorbent resin and a zeolite powder in the presence of water, followed by drying and grinding.

U.S. Pat. No. 6,124,391 discloses SAP particles containing 0.2 to 10 wt % of an inorganic powder, e.g., a clay, having improved anticaking properties, wherein more than 60 wt % of the particles are larger than 300 μm. Clay is added before, during, or after a surface crosslinking step.

WO 00/72958 discloses a process for producing a networked polymer/clay alloy for use in a personal care article. The process comprises the steps of:
  (a) preparing a monomer/clay mixture by mixing at least a monomer, clay particles, a crosslinking agent, and a mixing fluid in a vessel;
  (b) exposing the monomer/clay mixture to a polymerization initiator; and
  (c) polymerizing the monomer/clay mixture to form a networked polymer/clay alloy.

WO 01/13965 discloses water-absorbent polymers containing silicium-rich zeolites for odor control. The silicium-rich zeolites can be added to the monomer solution, to the SAP gel, or in the surface crbsslinking step.

WO 01/32117 discloses an SAP composition containing a partially neutralized SAP wherein at least 30% of the functional groups of the polymer are in free acid form, and a layered double hydroxide anionic clay, e.g., hydrotalcite clays. In the examples, the composites were prepared by powder/powder mixing.

WO 01/68156 discloses a hydrophilic swellable hydrogel-forming polymer containing alumosilicate and having enhanced permeability and improved odor-control properties. The alumosilicates can be added before, during, or after polymerization.

However, a need still exists for SAP-clay particles having improved fluid permeability when in the swollen state. The above-described compositions containing an SAP and an inorganic material, like a clay, have not met this need. Accordingly, the present invention is directed to improving the permeability and absorption rates of SAP particles by introducing a clay into the SAP hydrogel. It has been found that the addition of a clay to an SAP hydrogel prior to neutralizing the hydrogel facilitates drying of the hydrogel, and can significantly improve SAP performance with respect to rate of fluid absorption by a diaper core containing the SAP-clay particles, and fluid permeability through swollen SAP-clay particles.

Therefore, the present invention is directed to improving SAP absorption rate and permeability performance, without adversely affecting other fluid absorption and retention properties of the SAP particles, by the addition of a clay during the manufacturing process.

SUMMARY OF THE INVENTION

The present invention is directed to SAP particles and methods of manufacturing SAP particles. More particularly, the present invention is directed to SAP particles comprising a water-absorbing resin and a clay, and a method of manufacturing such SAP-clay particles.

One aspect of the present invention, therefore, is to provide a method of manufacturing SAP particles including the steps of polymerizing an aqueous monomer mixture containing an unneutralized monomer capable of providing an SAP, such as an $\alpha,\beta$-unsaturated carboxylic acid, like acrylic acid, and an internal crosslinking monomer to form an SAP hydrogel; comminuting the SAP hydrogel to form SAP hydrogel particles; admixing a clay with the SAP hydrogel particles; then neutralizing the SAP hydrogel-clay particles; and finally drying the SAP hydrogel-clay particles to provide dry SAP particles containing a clay.

Another aspect of the present invention is to provide a method of manufacturing SAP particles containing a clay by a solution polymerization process comprising (a) forming an aqueous monomer solution comprising an unneutralized $\alpha,\beta$-unsaturated carboxylic acid, a polyethylenically unsaturated polymerizable monomer as an internal crosslinking monomer, and a redox catalyst system and/or a thermal free radical initiator, (b) polymerizing monomers in the monomer solution a sufficient amount to form an SAP hydrogel having a free monomer content of less than 1000 ppm (parts per million), (c) comminuting the SAP hydrogel, e.g., extruding or gel chopping, to provide SAP hydrogel particles of desired particle size, (d) adding a clay to the SAP hydrogel particles, (e) comminuting the SAP hydrogel-clay mixture and dispersing the clay in the SAP hydrogel particles, (f) neutralizing the SAP hydrogel-clay particles to provide a DN (degree of neutralization) of about 50 to about 100, and (g) drying the SAP hydrogel-clay particles to provide dry SAP clay particles. The SAP and clay are present in a single particle, and a portion of the clay typically is present on the surface of the particles.

Another aspect of the present invention is to provide SAP-clay particles having a reduced amount of internal crosslinking monomer, and that are easier to handle and more readily dried than identical SAP particles that are free of a clay.

Another aspect of the present invention is to provide particles containing an SAP and a clay, and (a) having high fluid absorbance and retention properties and (b) a fast fluid acquisition rate and an excellent fluid permeability in the swollen state.

Still another aspect of the present invention is to provide a composition comprising discrete particles containing both an SAP and a clay, wherein the clay is selected from the group consisting of (a) a swelling clay, (b) a nonswelling clay, and (c) mixtures thereof, wherein the clay is added to an SAP hydrogel prior to neutralization.

In preferred embodiments of the present invention, the SAP-clay particles comprise a partially neutralized SAP, e.g., poly(acrylic acid) (PAA) or a poly(vinylamine) (PVAm), containing at least 25%, preferably at least 50%, and up to 100%, neutralized carboxyl groups or amino groups, and a nonswellable clay.

Yet another aspect of the present invention is to provide articles of manufacture containing SAP-clay particles of the present invention, for example, a diaper, a catamenial device, a feminine hygiene product, an adult incontinence product, general purpose wipes and cloths, and similar absorbent products. The SAP-clay particles are present in a core of the article of manufacture, and the core exhibits reduced fluid acquisition times, i.e., an increased fluid acquisition rate.

Further aspects and advantages of the present invention will become apparent to those skilled in the art from the following detailed description of the preferred embodiments, taken in conjunction with the examples and the appended claims.

DETAILED DESCRIPTION OF THE PREFERRED EMBODIMENTS

The present invention is directed to an absorbent particles comprising (a) an SAP and (b) a clay. The SAP and clay are present in a single particle, as opposed to an admixture of discrete SAP particles and discrete clay particles. In accordance with an important feature of the present invention, the particles contain about 50% to about 95%, and preferably about 60% to about 90%, by weight, of the SAP. To achieve the full advantage of the present invention, the particles contain about 65% to about 85%, by weight, of the SAP. Conversely, the particles contain about 5% to about 50%, and preferably about 10% to about 40%, by weight, of the clay. To achieve the full advantage of the present invention, the particles contain about 15% to about 35%, by weight, of the clay.

The SAP component of the SAP-clay particles are prepared by well-known continuous and discontinuous processes. The monomers comprising the SAP component of the SAP-clay particles typically are polymerized in aqueous solution to form an SAP hydrogel. However, the SAP component of the present particles can be prepared by any other method known to persons skilled in the art, like inverse suspension polymerization.

The monomers of the SAP component comprise an ethylenic monomer having a carboxylic acid substituent or a precursor to a carboxylic acid substituent, e.g., an α,β-unsaturated carboxylic acid or anhydride thereof, typically acrylic acid, or (meth)acrylonitrile or a (meth)acrylamide, or an ethylenic monomer having an amine substituent or a precursor to an amine substituent, e.g., N-vinyl acetamide. The monomers used in the polymerization are unneutralized, i.e., contain 90% or more, and typically 100%, of the carboxyl or amino groups in the free acid or free base form, respectively.

The product of the polymerization process is an SAP hydrogel, which is a water-swollen form of the SAP. Generally, the SAP hydrogel is subjected to a mechanical comminution, i.e., reduction of the particle size of the SAP hydrogel, for example, by chopping. Next, the SAP hydrogel particles are dried to remove water and provide dry SAP particles. The dry SAP particles then can be subjected to further mechanical means for particle size reduction and classification including chopping, grinding, and sieving. In embodiments wherein a surface crosslinking agent is used, the surface crosslinking agent is applied to the dried SAP particles. After application of the surface crosslinking agent, the SAP particles are subjected to conditions wherein the surface crosslinking agent reacts with a portion of the carboxyl or amino groups of the SAP to crosslink the surfaces of the SAP particles.

Particles of the present invention contain an SAP and a clay incorporated into a single particle. The particles can be prepared, for example, by a method comprising the steps of polymerizing at least one vinyl monomer capable of providing an SAP, e.g., an α,β-unsaturated carboxylic acid, in its unneutralized form to form a polymeric SAP hydrogel. The SAP hydrogel resulting from monomer polymerization is comminuted, then a clay, typically as an aqueous clay slurry, is added to the comminuted SAP hydrogel particles. The clay also can be added as solid particles or a powder. The SAP hydrogel and clay then can be intimately admixed, e.g., by extrusion, to disperse the clay in and on the hydrogel particles. The resulting unneutralized SAP-clay mixture then is neutralized using a suitable base, and finally comminuted, dried and sized, and optionally surface crosslinked to provide neutralized SAP-clay particles. Neutralization and comminution of the SAP-clay hydrogel particles can be performed simultaneously or sequentially. In preferred embodiments, the SAP-clay hydrogel particles are neutralized, then comminuted.

The SAP component of the SAP-clay particles is based on polymerized vinyl monomers, particularly α,β-unsaturated carboxylic acids, and the SAP component has the ability to absorb several times its weight of an aqueous liquid. The remainder of the specification is particularly directed to an SAP component based on acrylic acid. However, other vinyl monomers (e.g., vinyl amine and its precursors) and other α,β-unsaturated carboxylic acids, anhydrides, and carboxylic acid precursors can be employed to prepare an SAP useful in the absorbent particles of the present invention. In particular, SAP-clay particles of the present invention exhibit improved absorption of an aqueous fluid regardless of the identity of the α,β-unsaturated carboxylic acid or other vinyl monomer used to prepare the SAP. The present SAP-clay particles also have an improved fluid permeability through the fluid swollen particles, and have an improved dry feel of fluid swollen particles.

The SAP-clay particles of the present invention can be used in absorbent articles, such as diapers, catamenial devices, and adult incontinence products. The particles are especially useful in absorbing electrolyte-containing fluids, such as urine and blood.

Various embodiments of the present invention, and a nonlimiting description of the components of the present SAP-clay particles, follow.

Superabsorbent Polymer (SAP) Component

An SAP used in the SAP-clay particles of the present invention is limited only in that the SAP is capable of absorbing several times its weight of an aqueous fluid and swells to form a hydrogel. The SAP can be an acidic water-absorbing resin or a basic water-absorbing resin. Monomers useful in the preparation of an SAP are disclosed in U.S. Pat. No. 5,149,750 and WO 01/68156, each incorporated herein by reference. The SAP component of the present SAP-clay particles comprises an acidic or a basic water-absorbing resin neutralized about 25% to about 100%, i.e., has a degree of neutralization (DN) of about 25 to about 100, after incorporation of a clay into the SAP hydrogel.

The SAP can be anionic (an acidic water-absorbing resin) or cationic (a basic water-absorbing rein) in nature. The anionic SAPs are based on an acidic water-absorbing resin. The anionic SAPs, either strongly acidic or weakly acidic, can be any resin that acts as an SAP in its neutralized form. The acidic resins typically contain a plurality of carboxylic acid, sulfonic acid, phosphonic acid, phosphoric acid, and/or sulfuric acid moieties.

A preferred SAP is an acidic water-absorbing resin neutralized 25% to 100%. The acidic water-absorbing resin can be a single resin or a mixture of resins. The acidic resin can be a homo-polymer or a copolymer. The identity of the acidic water-absorbing resin is not limited as long as the resin is capable of swelling and absorbing at least ten times its weight in water, when in a neutralized form.

The acidic water-absorbing resin typically is a lightly crosslinked acrylic resin, such as lightly crosslinked poly(acrylic acid). The lightly crosslinked acidic resin typically is prepared by polymerizing an acidic monomer containing an acyl moiety, e.g., acrylic acid, or a moiety capable of providing an acid group, i.e., acrylonitrile, in the presence of an internal crosslinking monomer, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units.

Ethylenically unsaturated carboxylic acid and carboxylic acid anhydride monomers useful in the acidic water-absorbing resin include acrylic acid, methacrylic acid, ethacrylic acid, α-chloroacrylic acid, α-cyanoacrylic acid, β-methylacrylic acid (crotonic acid), α-phenylacrylic acid, β-acryloxy-propionic acid sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, furmaric acid, tricarboxyethylene, and maleic anhydride. Acrylic acid is the most preferred ethylenically unsaturated carboxylic acid for preparing the SAP.

Ethylenically unsaturated sulfonic acid monomers include aliphatic and aromatic vinyl sulfonic acids, such as vinyl sulfonic acid, allyl sulfonic acid, vinyl toluene sulfonic acid, styrene sulfonic acid, acrylic and methacrylic sulfonic acids, such as sulfoethyl acrylate, suffoethyl meth-acrylate, sulfopropyl acrylate, sulfopropyl meth-acrylate, 2-hydroxy-3-methacryloxypropyl sulfonic acid, and 2-acrylamide-2-methylpropane sulfonic acid. Phosphate-containing acidic resins are prepared by homopolymerizing or copolymerizing ethylenically unsaturated monomers containing a phosphoric acid moiety, such as methacryloxy ethyl phosphate. An extensive list of suitable SAP-forming monomers can be found in U.S. Pat. No. 4,076,663, incorporated herein by reference.

The anionic SAPs can be, for example, a poly(acrylic acid), a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinyl-phosphonic acid), a poly(vinylphosphoric acid), a poly(vinylsulfuric acid), a sulfonated polystyrene, and mixtures thereof. The preferred anionic SAP is a poly(acrylic acid).

The polymerization of acidic monomers, and copolymerizable monomers, if present, most commonly is performed by free radical processes in the presence of a polyfunctional internal crosslinking monomer. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than about, 20%, preferably less than about 10%, and most preferably about 0.01% to about 7%.

An internal crosslinking monomer most preferably is used in an amount of less than about 7 wt %, and typically about 0.1 wt % to about 5 wt %, based on the total weight of monomers. In accordance with an important feature of the present invention, the incorporation of a clay into the SAP hydrogel prior to neutralization allows the amount of internal crosslinking monomer to be reduced compared to the amount of internal crosslinking monomer required in an SAP absent a clay. In general, a low amount of internal crosslinking monomer provides an SAP hydrogel that is difficult to handle, and especially to comminute and dry. The addition of a clay to an SAP hydrogel prior to neutralization allows the amount of internal crosslinking monomer to be decreased by about 10% to about 25% compared to the amount of internal crosslinking monomer used in an SAP hydrogel free of a clay, without adversely affected handling and drying of the SAP particles.

Examples of internal crosslinking monomers include, but are not limited to, polyacrylic (or polymethacrylic) acid esters represented by the following formula (I),

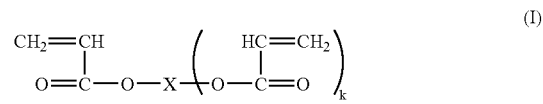

wherein x is ethylene, propylene, trimethylene, cyclohexyl, hexamethylene, 2-hydroxypropylene, —(CH$_2$CH$_2$O)$_n$CH$_2$CH$_2$—, or

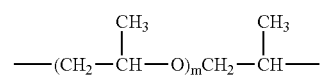

n and m, independently, are an integer 5 to 40, and k is 1 or 2; and bisacrylamides, represented by the following formula (II),

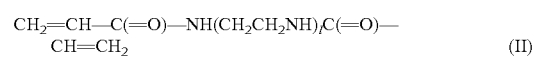

wherein l is 2 or 3.

The compounds of formula (I) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or meth-acrylic acid. The compounds of formula (II) are obtained by reacting polyalkylene polyamines, such as diethylenetriamine and triethylenetetramine, with acrylic acid. Specific crosslinking monomers are disclosed in U.S. Pat. No. 6,222,091, incorporated herein by reference. Especially preferred crosslinking agents are pentaerythritol triallyl ether, pentaerythritol triacrylate, N,N'-methylenebisacrylamide, N,N'-methylenebismeth-acrylamide, ethylene glycol dimethacrylate, and trimethylolpropane triacrylate.

Analogous to the acidic resin, a basic water-absorbing resin, i.e., cationic SAP, useful in the present SAP-clay particles can be a strong or weak basic water-absorbing resin. The basic water-absorbing resin can be a single resin or a mixture of resins. The basic resin can be a homopolymer or a copolymer. The identity of the basic resin is not limited as long as the basic resin is capable of swelling and absorbing at least 10 times its weight in water, when in a charged form. The weak basic resin preferably is present in its cationic form, i.e., about 25% to 100% of the basic moieties, e.g., amino groups, are present in a charged form. The strong basic resins typically are present in the hydroxide (OH) or bicarbonate ($HCO_3$) form.

The basic water-absorbing resin typically is a lightly crosslinked resin, such as a poly(vin-ylamine) or a poly (dialkylaminoalkyl(meth)acryl-amide). The basic resin also can be, for example, a lightly crosslinked polyethylenimine, a poly(allylamine), a poly(allylguanidine), a poly(dimethyidiallylammonium hydroxide), a quaternized poly-styrene derivative, a guanidine-modified polystyrene, a quaternized poly((meth)acrylamide) or ester analog. See U.S. Pat. No. 6,235,965, incorporated herein by reference. The lightly crosslinked basic water-absorbing resin can contain other copolymerizable units and is crosslinked using an internal crosslinking momomer, as set forth above with respect to the acidic water-absorbing resin. Preferred basic resins include a poly(vinylamine), polyethylenimine, poly(vinylguanidine), poly(dimethylaminoethyl acrylamide) (poly(DAEA)), and poly(dimethylaminopropyl methacrylamide) (poly(D-MAPMA)).

A basic water-absorbing resin used in the present SAP particles typically contains an amino or a guanidino group. Accordingly, a water-soluble basic resin also can be crosslinked in solution by suspending or dissolving an uncrosslinked basic resin in an aqueous or alcoholic medium, then adding a di- or polyfunctional compound capable of cross-linking the basic resin by reaction with the amino groups of the basic resin. Such crosslinking agents are disclosed in U.S. Pat. No. 6,235,956, incorporated herein by reference. Crosslinking agents also are disclosed in Pinschmidt, Jr. et al. U.S. Pat. No. 5,085,787, incorporated herein by reference, and in EP 450 923. Preferred crosslinking agents are ethylene glycol diglycidyl ether (EGDGE), a water-soluble diglycidyl ether, and a dibromoalkane, an alcohol-soluble compound.

Copolymerizable monomers for introduction into the acidic resin or the basic resin, include, but are not limited to, ethylene, propylene, isobutylene, $C_{1-4}$alkyl acrylates and methacrylates, vinyl acetate, methyl vinyl ether, and styrenic compounds having the formula:

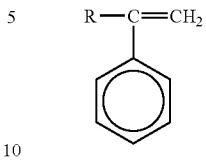

wherein R represents hydrogen or a $C_{1-6}$alkyl group, and wherein the phenyl ring optionally is substituted with one to four $C_{1-4}$alkyl or hydroxy groups.

Suitable $C_{1-4}$alkyl acrylates include, but are not limited to, methyl acrylate, ethyl acrylate, isopropyl acrylate, n-propyl acrylate, n-butyl acrylate, and the like, and mixtures thereof. Suitable $C_{1-4}$alkyl methacrylates include, but are not limited to, methyl methacrylate, ethyl methacrylate, isopropyl methacrylate, n-propylmethylmethacrylate, n-butyl methacrylaite, and the like, and mixtures thereof or with $C_{1-4}$alkyl acrylates. Suitable styrenic compounds include, but are not limited to, styrene, α-methylstyrene, p-methylstyrene, t-butyl styrene, and the like, and mixtures thereof or with $C_{1-4}$alkyl acrylates and/or methacrylates.

Any polymerization initiator known for use in preparing SAPs can be used. Examples of useful initiators are redox and thermal initiators, such as those disclosed in U.S. Pat. No. 6,359,049, incorporated herein by reference. The redox and thermal initiators can be used singly or in suitable combination. Of these, especially preferred initiators are a redox initiator comprising ammonium persulfate and sodium hydrogen sulfite, and azo initiators, such as azobisisobutyronitrile and 2,2'-azobis(2-amidinopropane)di-hydrochloride, commercially available under the tradename V-50 from Wako Chemicals U.S.A., Inc., Richmond, Va. The initiator typically is used in an amount, calculated as solids, of about 0.1% to about 10%, based on the weight of the acrylic acid monomer, preferably about 0.5% to about 5%, based on the weight of the monomer. Depending on the amount and kind of the initiator, the initiator optionally can be used together with isopropyl alcohol, an alkyl mercaptan, or other chain transfer agent to control the molecular weight of the poly(acrylic acid).

Ultraviolet (UV) light also can be used to effect polymerization of acrylic acid. UV light can be used in conjunction with a redox initiator and/or a free radical initiator. When UV light is utilized in the polymerization step, a photoinitiator also is added to the reaction mixture in an amount well known to persons skilled in the art. Suitable photoinitiators include, but are not limited to, 2-hydroxy-1-[4-(hydroxyethy-oxy)phenyl]-2-methyl-1-propanone, which is commercially available from Ciba Additives of Hawthorne, N.Y., as IRGACURE® 2959, and 2-hydroxy-2-methyl-1-phenyl-1-propanone, which also is commercially available from Ciba Additives as DAROCUR® 1173.

Industrial processes useful for preparing the SAP component of the SAP-clay particles include all processes customarily used to synthesize SAPs, as described, for example, in Chapter 3 of "Modern Superabsorbent Polymer Technology," F. L. Buchholz and A. T. Graham, Wiley-VCH (1998). A suitable process for polymerizing the acrylic acid is aqueous solution polymerization, wherein an aqueous solution containing acrylic acid and polymerization initiator is subjected to a polymerization reaction and a crosslinking reaction by the addition of an internal crosslinking monomer, such as methylenebisacrylamide.

As previously noted, the polymerization reaction proceeds rapidly to yield a highly viscous hydrogel that is extruded, for example, onto a flat surface such as a continuously moving conveyor belt. The SAP hydrogel then is comminuted, and the clay is added to, and intimately admixed with, the comminuted SAP hydrogel particles. This intimate admixture then is neutralized with a suitable base, for example, with sodium carbonate, and optionally comminuted, to provide SAP-clay hydrogel particles having a degree of neutralization (DN) of about 25% to about 100%, preferably about 50% to about 85%, more preferably about 65% to about 80%. Neutralization and comminution after clay addition can be performed simultaneously or sequentially.

After neutralization, the viscous SAP-clay hydrogel particles are dehydrated (i.e., dried) to obtain SAP-clay particles in a solid or powder form. The dehydration step can be performed, for example, by heating the viscous SAP-clay hydrogel particles at a temperature of about 120° C. for about 1 to about 2 hours in a forced-air oven or by heating the viscous hydrogel overnight at a temperature of about 60° C. The dried SAP-clay particles thereafter can be optionally surface crosslinked with a surface crosslinker, like ethylene glycol diglycidyl ether (i.e., "EGDGE") or propylene glycol.

A preferred SAP is neutralized poly(acrylic acid), i.e., PAA. A suitable PAA can be prepared as follows. This disclosure is directed primarily to the preparation of poly (acrylic acid) (i.e., PAA), but other acidic and basic water-absorbing resins can be manufactured by an identical or similar method.

EXAMPLE 1

In general, PAA can be prepared from an aqueous solution containing about 10% to about 40%, preferably about 15% to about 35%, more preferably about 20% to about 30%, and most preferably about 25% to about 28% by weight, by weight, acrylic acid, with an appropriate amount of internal crosslinking monomer. A PAA so obtained, after admixture with a clay, is neutralized with sodium carbonate, potassium carbonate, ammonium carbonate, sodium hydroxide, or a mixture thereof, to DN=60-95.

In particular, a solution containing 25% by weight acrylic acid, 0.07 mole percent methylenebisacrylamide, appropriate levels of initiators (2,2'-azobis(2-amidinopropane)dihydrochloride and sodium persulfate), at an initiator temperature of 18° C., yielded a PAA which, when neutralized with sodium carbonate powder to DN=75 percent and then dried, milled, sized, and post-modified by surface crosslinking, yielded a PAA with an average gel volume of 41.2 gm/gm, an absorption under load (AUL) of 34.1 gm/gm (0.28 psi load) and 27.1 gm/gm (0.7 psi load), 7.7 wt % extractables, and a residual acrylic acid content of 140 parts per million (ppm).

In accordance with an important feature of the present invention, clay particles or a clay slurry is added to a PAA hydrogel prior to neutralization.

SAP-clay particles of the present invention optionally are surface crosslinked or annealed to improve the absorption properties of the particles. Surface crosslinking or annealing of an SAP is known in the art, as set forth in U.S. Pat. No. 6,222,091, incorporated herein by reference, which discloses compounds and conditions for surface crosslinking and/or annealing an acidic or a basic SAP.

Surface crosslinking is achieved by contacting an acidic water-absorbing resin, or a basic water-absorbing resin, with a solution of a surface crosslinking agent to wet predominantly only the outer surfaces of the SAP-clay particle. Surface crosslinking and drying of the SAP-clay particles then is performed, preferably by heating at least the wetted surfaces of the SAP-clay particles.

In addition to, or in lieu of, surface treating the SAP-clay particles, the SAP-clay particles can be annealed to improve water absorption and retention properties of the SAP. Heating SAP-clay particles for a sufficient time at a sufficient temperature above the Tg (glass transition temperature) of the resin improves the absorption properties of the resin.

The following Example 2 illustrates an additional nonlimiting example of an SAP that can be used as the SAP component of the SAP-clay particles of the present invention.

EXAMPLE 2

To a suitable reactor was added 800 parts of acrylic acid, 4 parts of tetraallyloxyethane, 1818.2 parts of 2.2 percent oxidized starch in water, and 1347.8 parts of water. Nitrogen was bubbled through the resulting solution, and the temperature was lowered to 100° C. When the dissolved oxygen was reduced below 1 ppm, the following catalysts were added in the listed order: 2.4 parts of 2,2-azobisamidinopropane dihydrochloride in 10 parts of water; 0.2 parts of ascorbic acid in 10 parts of water; 2.29 parts of 35 percent hydrogen peroxide in 10 parts of water.

After a short induction period, polymerization began and a peak temperature of 65-70° C. was reached in two hours. The PAA gel was retained in an insulated container for three hours to reduce residual monomer below 1000 ppm.

Clay Component

A clay useful in the present SAP-clay particles can be a swelling or a nonswelling clay. Swelling clays have the ability to absorb water and are swellable, layered organic materials. Suitable swelling clays include, but are not limited to, montmorillonite, saponite, nontronite, laponite, beidelite, hectorite, sauconite, stevensite, vermiculite, volkonskoite, magadite, medmontite, kenyaite, and mixtures thereof.

Preferably, the swelling clay is a smectite or vermiculite clay. More preferably, the clay is a smectite clay. Examples of suitable smectites include, but are not limited to, montmorillonite (often referred to as bentonite), beidelite, nontronite, hectorite, saponite, sauconite, and laponite. Bentonite is a naturally occurring combination of clay particles, rich in montmorillonite and also including other smectites, as well as nonclay mineral constituents.

Suitable nonswelling clays include, without limitation, kaolin minerals (including kaolinite, dickite, and nacrite), serpentine minerals, mica minerals (including illite), chlorite minerals, sepolite, palygorskite, bauxite, and mixtures thereof.

The clay also can be an organophilic clay. As used here and hereafter, the term "organophilic" is defined as the property of a compound to absorb at least its own weight, and preferably many times its own weight, of an organic, water-immiscible compound. An organophilic compound optionally can absorb water or a water-miscible compound.

The terms "organophilic clay" and "organoclay" are used interchangeably herein to refer to various types of clay, e.g., smectites, that have organoammonium ions substituted for metal cations (e.g., sodium and/or potassium) present between the clay layers. The term "organoammonium ion"

refers to a substituted ammonium ion wherein one or more hydrogen atoms are replaced by an aliphatic or aromatic organic group. The organoclays, therefore, are solid compounds that have an inorganic component and an organic component.

The preferred clay substrates of an organophilic clay are the smectite-type clays, particularly smectite-type clays that have a cation exchange capacity of at least 75 milliequivalents per 100 grams of clay. Useful clay substrates include, but are not limited to, the naturally occurring Wyoming variety of bentonite and similar clays, and hectorite, which is a magnesium-lithium silicate clay. The clays preferably first are converted to the sodium form if they are not already in this form. This conversion can be effected by a cation exchange reaction using a soluble sodium compound by methods well known in the art. Smectite-type clays prepared synthetically also can be utilized, for example, montmorillonite, bentonite, beidelite, hectorte, saponite, and stevensite. Other useful clay substrates include nontronite, illite, attapulgite, and a fuller's earth.

Organoclays useful in the present invention also include those set forth in Hauser U.S. Pat. No. 2,531,427, incorporated herein by reference. These organoclays are modified clays that exhibit, in an inorganic liquid, some of the properties an untreated clay exhibits in water. For example, the ability to swell in organic liquids and form stable gels and colloidal dispersions.

Generally, the organoammonium ion substituted onto the clay substrate has an organic group that ranges from an aliphatic hydrocarbon moiety having 1 to 24 carbon atoms to an aromatic organic moiety, such as a benzyl group that can have a variety of groups substituted on the phenyl ring. The number of benzyl versus aliphatic hydrocarbon moieties substituted on the ammonium ion can vary from 3 to 0 aromatic moieties per aliphatic moiety (i.e., dimethyl dioctadecyl 0:2, methyl benzyl dioctadecyl 1:2, dibenzyl dioctabenzyl 2:2, tribenzyl octadecyl 3:1, and methyl dibenzyl octadecyl 2:1). The amount of organoammonium ion substituted onto the clay substrate typically is about 0.5% to about 50%, by weight of the organophilic clay.

Preferred organoclays comprise one or more of the following types of organoammonium cation-modified montmorillonite clays:

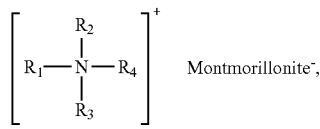

wherein $R_1$ is an alkyl group having at least 20, and up to, for example, 24 carbon atoms, and preferably having a chain length of 12 to 18 carbon atoms; $R_2$ is hydrogen, benzyl, or an alkyl group having at least 10, and up to, for example, 24 carbon atoms, and preferably 12 to 18 carbon atoms; and $R_3$ and $R_4$, independently, are a lower alkyl group, i.e., an alkyl group containing carbon chains of 1 to 4 atoms, and preferably methyl groups.

Other useful organoclays include benzyl organoclays, such as dimethyl benzyl (hydrogenated tallow) ammonium bentonite; methyl benzyl di(hydrogenated tallow) ammonium bentonite; and more generally organoammonium-cation modified montmorillonite clays represented by the formula:

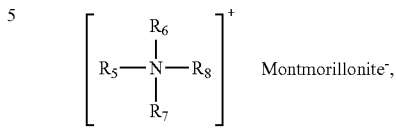

wherein $R_5$ is $CH_3$ or $C_6H_5CH_2$; $R_6$ is $C_6H_5CH_2$; and $R_7$ and $R_8$, independently, are alkyl groups containing long chain alkyl radicals having 14 to 22 carbon atoms, and most preferably where 20% to 35% of said long chain alkyl radicals contain 16 carbon atoms and 60% to 75% of said long chain alkyl radicals contain 18 carbon atoms.

The montmorillonite clays that can be so modified are the principal constituents of bentonite rock, and have the chemical compositions and characteristics described, for example, in Berry & Mason, "Mineralogy," pp. 508-509 (1959). Modified montmorillonite clays of this type (i.e., organoclays) are commercially available from Southern Clay Products, Inc., Gonzales, Tex., under trade designations such as CLAYTONE® 34 and 40, and from NL Industries, Inc., New York, N.Y., under trade designations such as BENTONE® 27, 34, and 38. Other organoclays useful in the invention are the higher dialkyl dimethyl ammonium organoclays, such as dimethyl di-(hydrogenated tallow) ammonium bentonite; the benzyl ammonium organoclays, such as dimethyl benzyl (hydrogenated tallow) ammonium bentonite; and ethylhydroxy ammonium organoclays, such as methyl bis(2-hydroxyethyl) octadecyl ammonium bentonite. Examples of nonswelling organophilic clays are bentonite clays treated with an amine containing three to eight carbon atoms, e.g., propylamine, butylamine, or octylamine.

Other commercially available clays include ULTRA-GLOSS® clays (hydrous kaolin) from Engelhard Corporation, Iselin, N.J.; Purified Clay from Nanocor Technologies, Arlington Heights, Ill.; and HYDROGLOSS® from Huber, Atlanta, Ga.

Another suitable clay component comprises the aluminosilicates. Useful aluminosilicates are nonzeolite silicates wherein a portion of the silicon atoms are replaced by aluminum atoms. Because the aluminum atom has one positive nuclear charge less than the silicon atom, every aluminum atom replacing a silicon atom increases the negative charge of the lattice anion by one unit. Additional cations, therefore, are needed to neutralize the molecule. Consequently, in addition to aluminum atoms, aluminosilicates can include additional metal atoms, e.g., alkali and alkaline earth metal atoms, such as sodium, potassium, magnesium, calcium, iron, and zinc. Useful aluminosilicates have a layered structure. In accordance with the present invention, both naturally occurring and synthetic aluminosilicates are useful.

Naturally occurring aluminosilicates include the micas. Micas are infinite sheet silicates containing layers of tetrahedral. An example of a useful sheet-like aluminosilicate for the purposes of the invention is the synthetic aluminosilicate saponite. Synthetic saponite (CAS No. 1319-41-1) is commercially available as a white, odorless powder and has the formula

Examples of useful naturally occurring micas are muscovite, biotite, phlogopite, lepidolite, zinnwaldite, paragonite, and montmorillonite.

A clay does not perform, like an SAP with respect to absorbing and retaining large amounts of an aqueous fluid. A clay typically is referred to, and considered, as a diluent for SAP particles in an attempt to improve one or more properties of the SAP. It also is expected that other SAP properties would be adversely affected by diluting an SAP with a clay. However, as demonstrated hereafter, after adding a clay to SAP particles, the beneficial properties associated with an SAP are diminished to a substantially lower degree than expected, while other beneficial properties are improved.

Surprisingly, it has been found that the absorption and retention properties of SAP-clay particles can be improved by providing discrete particles containing both an SAP and a clay, wherein the clay is added to an SAP hydrogel prior to SAP neutralization. In particular, incorporating the resulting SAP-clay particles into a diaper core provides cores having improved fluid acquisition rates.

In addition, the presence of a clay on the surface of the SAP-clay particles facilitates drying of the SAP-clay hydrogel particles, and provides SAP particles that are easier to handle during production of absorbent articles. These features allow a reduction in the amount of internal crosslinking monomer in the SAP, with a corresponding improvement in absorption properties. A reduction in the amount of internal crosslinker in the SAP component is possible because of an ability to readily handle and manipulate, and easily dry, the SAP-clay hydrogel particles.

It is theorized, but not relied upon herein, that because an unneutralized SAP hydrogel absorbs aqueous fluids more slowly than a neutralized SAP hydrogel, a clay slurry also is absorbed more slowly by an unneutralized SAP hydrogel. Therefore, the clay is distributed more homogeneously on and into the unneutralized SAP hydrogel particles. A diaper having a core containing the present dry SAP-clay particles, therefore, exhibits an improved acquisition rate, fluid permeability, and dry feel after fluid absorption.

The following Example 3 illustrates a general method of manufacturing SAP-clay particles of the present invention.

EXAMPLE 3

Acrylic acid (292 grams) and pentaerythritol triallyl ether (0.800 grams) are admixed. Then, deionized water (783 grams) is added to the mixture, and stirring is continued. The resulting solution is cooled to about 10° C., then 2-hydroxy-2-methyl-1-phenylpropane (DAROCUR® 1173) (0.200 grams) and sodium persulfate (5.99 grams) are added with stirring. The resulting solution is poured into a 4 inch×8 inch glass dish and polymerized for 12.5 minutes under UV light (UV intensity=20 mW/cm$^2$). The resulting gel is extruded through a KitchenAid meat grinder, then 5-50% ULTRAGLOSS® 90 clay (wt % based on acrylic acid (boaa)) is added to the hydrogel, followed by two extrusions. Next, 159.15 grams of sodium carbonate is added to the clay-containing hydrogel, then the clay-containing hydrogel is extruded to neutralize the PAA. The resulting neutralized SAP-clay hydrogel is dried at 150° C. for one hour, then milled and sized to 180-710 μm. The dry SAP particles containing the clay then is surface crosslinked with 1000 ppm EGDGE by curing at 150° C. for 1 hour.

As set forth in Example 3, preferred SAP-clay particles of the present invention are surface crosslinked. Surface crosslinking is performed in a conventional manner using dried, ground, and classified SAP-clay particles of the present invention. Surface crosslinking is achieved by applying polyfunctional compounds capable of reacting with the functional groups of the SAP, typically in the form of an aqueous solution, to the surface, of the dry SAP-clay particles. The aqueous solution can contain water-miscible organic solvents, such as methanol, ethanol, isopropyl alcohol, or acetone, for example.

Suitable surface crosslinkers include, but are not limited to, di- or polyglycidyl compounds, such as diglycidyl phosphonates, ethylene glycol diglycidyl ether, and bischlorohydrin ethers of polyalkylene glycols; alkoxysilyl compounds; polyaziridines based on polyethers or substituted hydrocarbons, for example, bis-N-aziridinomethane; polyamines or polyamidoamines and their reaction products with epichlorohydrin; polyols, such as ethylene glycol, 1,2-propanediol, 1,4-butanediol, glycerol, methyltriglycol, polyethylene glycols having an average molecular weight $M_w$ of 200-10,000, di- and polyglycerol, pentaerythritol, sorbitol, the ethoxylates of these polyols and their esters with carboxylic acids orrcarbonic acid such as ethylene carbonate or propylene carbonate; carbonic acid derivatives, such as urea, thiourea, guanidine, dicyandiamide, 2-oxazolidinone and its derivatives, bisoxazoline, polyoxazolines, di- and polyisocyanates; di- and poly-N-methylol compounds such as, for example, methylenebis(N-methylolmethacrylamide) or melamine-formaldehyde resins; compounds having two or more blocked isocyanate groups such as, for example, trimethyl-hexamethylene diisocyanate blocked with 2,2,6,6-tetramethylpiperidin-4-one.

Particularly suitable surface crosslinkers are di- or polyglycidyl compounds, such as ethylene glycol diglycidyl ether. See U.S. Pat. No. 6,159,591, incorporated herein by reference, for additional surface crosslinking agents for anionic and cationic SAPs, and method of surface crosslinking and annealing SAP particles.

As illustrated in the following examples, comparative examples, and tests, the present invention provides SAP-clay particles having improved fluid acquisition rates and permeability of a fluid through swollen SAP particles. As an additional benefit, a portion of the clay remains on the surface of the dried SAP-clay particles to act as a processing aid, which facilitates handling of the SAP particles in the manufacture of absorbent articles, especially in humid environments and when the amount of internal crosslinking agent is low.

The following examples, comparative examples, and test results illustrate the new and unexpected results achieved by the addition of a clay to an SAP hydrogel prior to neutralization and drying of the hydrogel.

EXAMPLE 4

Under adiabatic conditions, a 5 liter wide-neck cylindrical reaction flask was charged with 2902 g (grams) of deionized water cooled to 15° C., 1040 g of acrylic acid, and 5.72 g of pentaerythritol triallyl ether. Nitrogen gas ($N_2$) was bubbled through the monomer solution (about 2 liters/min for about 20 min) to reduce the oxygen ($O_2$) content. At 1.5 ppm $O_2$, a solution of 0.52 g 2,2'-azobis(2-amidinopropane) dihydrochloride in 25 g of deionized water was added. After bubbling further $N_2$, and at an $O_2$ content of 1.3 ppm, 0.165 g of 35% $H_2O_2$ diluted with 12 g of deionized water, was added, and finally, at an $O_2$ content of 1.0 ppm, 0.0208 g of ascorbic acid dissolved in 15 g of deionized water was added. During the ensuing polymerization, the reaction temperature rose to about 75° C., and provided a solid gel that subsequently was subjected to mechanical comminution. The comminuted gel (1000 g) was admixed with 8 g of a synthetic trioctahedral sheet silicate bearing the mineralogical designation saponite (SKS-20 from HOECHST AG) suspended in 210.8 g of water. Next, a sufficient amount of 50% aqueous sodium hydroxide solution to provide a 73 mol % neutralized poly(acrylic acid) was added, and the hydrogel was passed twice through a mixing extruder. The resulting neutralized hydrogel-clay particles were dried at about 150° C., then ground and sieved.

Twenty grams of the SAP-clay particles were sprayed with a homogeneous solution containing 0.5 g 1,2-propanediol, 0.5 g water, 0.02 g EGDGE, and 0.015 of aluminum sulfate in a powder mixing assembly (WARING blender), and heated at 140° C. for 60 minutes, to surface crosslink the SAP-clay particles.

EXAMPLE 5

An aqueous monomer mixture containing 27 wt % acrylic acid, 0.09 wt % methylenebisacrylamide based on acrylic acid (boaa), 0.28 wt % sodium persulfate boaa, 0.075 wt % DAROCURE® 1173 boaa, and 0.025 wt % IRGACURE® 651 was prepared, then cooled to 15° C. The resulting monomer mixture then was polymerized for 12.5 minutes under a UV light (UV intensity=20 mW/cm$^2$). The resulting PAA hydrogel was extruded through a KitchenAid Model K5SS mixer fitted with a meat grinder attachment. Then varying amounts of a clay slurry (ULTRA WHITE® 90 clay slurry from Engelhard Industries, containing 70 wt % kaolin clay) were added to the PAA hydrogel, followed by two extrusions. Next, sodium carbonate was added to the clay-containing PAA hydrogel to neutralize the acrylic acid groups to 75 mol %, followed by two additional extrusions. The hydrogel consistency was evaluated visually by the following ranking:

1: Immediately after chopping, hydrogel particles are separated, hydrogel is "fluffy" and remains in this state after a holding time of 10 minutes.
2: Immediately after chopping, hydrogel particles are separated, hydrogel is "fluffy," but after a holding time of 10 minutes, hydrogel particles adhere to each other.
3: Immediately after chopping, hydrogel particles adhere to each other.

| Amount of clay (in wt %) added to the PAA (boaa) | Hydrogel consistency |
| --- | --- |
| 0.0 | 3 |
| 2.5 | 2-3 |
| 5.0 | 2 |
| 10.0 | 1-2 |
| 15.0 | 1 |
| 20.0 | 1 |

COMPARATIVE EXAMPLE 1

Example 5 was repeated, except the PAA hydrogels first were neutralized with sodium carbonate, then varying amounts of clay slurry were added to the neutralized PAA hydrogel. The hydrogel consistency also was evaluated visually using the ranking set forth in Example 5.

| Amount of clay (in wt %) added to the neutralized gel (boaa) | Gel consistency |
| --- | --- |
| 0.0 | 3 |
| 2.5 | 3 |
| 5.0 | 3 |
| 10.0 | 2-3 |
| 15.0 | 2-3 |
| 20.0 | 2 |

Comparative Example 1 shows that adding a clay to an SAP hydrogel after neutralization adversely affects hydrogel consistency, which in turn adversely affects handling of the SAP-clay hydrogel, especially comminuting the hydrogel into hydrogel particles and drying.

COMPARATIVE EXAMPLE 2

An aqueous monomer mixture containing 27 wt % acrylic acid, 0.09 wt % methylenebisacrylamide boaa, 0.28 wt % sodium persulfate boaa, 0.075 wt % of DAROCURE® 1173 boaa, and 0.025 wt % IRGACURE® 651, and varying amounts of ULTRA WHITE® 90 clay (added to the monomer mixture as an aqueous 70 wt % slurry) was prepared; then cooled to 15° C. The resulting monomer mixture then was polymerized for 12.5 minutes under a UV light (UV intensity=20 mW/cm$^2$). The consistency of the polymerized solution was as follows:

| Amount of clay (in wt %) added to the monomer mixture (boaa) | Consistency of the polymerized solution |
| --- | --- |
| 0.0 | Clear gel, not slimy |
| 2.5 | Slimy gel |
| 5.0 | Not completely gelled |
| 10.0 | Viscous solution |
| 15.0 | Viscous solution |
| 20.0 | Viscous solution |

Comparative Example 2, wherein a clay slurry is added to the monomer mixture prior to polymerization, shows that even a low weight percent of a clay added to the monomer mixture adversely affects the polymerization process. It is theorized, but not relied upon, that the presence of a clay in the monomer mixture interferes with the polymerization process by absorbing a portion of the UV energy applied to effect the polymerization.

Example 5 and Comparative Examples 1 and 2, therefore, illustrate the advantages achieved by adding a clay to an SAP hydrogel after polymerization and prior to neutralization.

EXAMPLE 6

An aqueous monomer mixture containing 27 wt % acrylic acid, 0.2 wt % pentaerythritol triacrylate boaa, 0.28 wt % of sodium persulfate boaa, 0.075 wt % DAROCURE® 1173 boaa, and 0.025 wt % IRGACURE® 651 was prepared, then cooled to 15° C. The resulting monomer mixture then was polymerized for 12.5 minutes under a UV light (UV) intensity=20 mW/cm$^2$). The resulting PAA hydrogel was extruded through a KitchenAid Model K5SS mixer fitted with a meat grinder attachment. Then varying amounts of ULTRA WHITE® 90 clay slurry containing 70 wt % kaolin clay were added to the PAA hydrogel, followed by two extrusions. Next, sodium carbonate was added to neutralize the acrylic acid groups 75 mol %, and water was added to adjust the solids content of the clay-containing PAA hydrogel to 30 wt %, followed by two addition extrusions. Immediately after chopping, the hydrogels were dried using a band dryer simulator, and the water evaporation rate was determined. The following conditions were chosen for the band dryer simulator experiments:

| Gel bed depth: | 40 mm |
|---|---|
| Air temperature: | 180° C. |
| Air speed: | 2.0 m/s |
| Final moisture content of gel: | .0 wt % |

| Amount of clay (in wt %) added to the PAA hydrogel (boaa) | Water evaporation rate (in kg/m$^2$h) |
|---|---|
| 0 | 72 |
| 5 | 85 |
| 10 | 100 |
| 15 | 114 |
| 20 | 128 |
| 30 | 140 |

COMPARATIVE EXAMPLE 3

An aqueous monomer mixture identical to Example 6 was prepared, then cooled to 15° C. The monomer mixture then was polymerized for 12.5 minutes under a UV light (UV intensity=20 mW/cm$^2$). The resulting PAA hydrogel was extruded through a KitchenAid Model K5SS mixer fitted with a meat grinder attachment. Then, sodium, carbonate was added to the hydrogel to neutralize the acrylic acid groups to 75 mol % followed by TWX extrusions. Next, varying amounts of ULTRA WHITE® 90 clay slurry and water were added to adjust the solids content of the clay-containing PAA hydrogel to 30 wt %, followed by two additional extrusions. Immediately after chopping, the hydrogel particles were dried using a band dryer simulator, and the water evaporation rate was determined. The conditions for the band dryer simulator experiments were identical to those of Example 6.

| Amount of clay (in wt %) added to the neutralized hydrogel (boaa) | Water evaporation rate (in kg/m$^2$h) |
|---|---|
| 0 | 75 |
| 5 | 73 |
| 10 | 86 |

The drying rate of the SAP-clay hydrogel particles of Example 6 is substantially faster then the drying rate of hydrogel particles of Comparative Example 3, especially as the weight percent of clay in the PAA hydrogel increases. Example 6 and Comparative Example 3 further illustrate the advantage of adding a clay to an SAP hydrogel prior to SAP neutralization.

EXAMPLE 7

An aqueous monomer mixture containing 25 wt % acrylic acid, 0.4 wt % ethoxylated trimethylolpropane triacrylate boaa, 0.28 wt % sodium persulfate boaa, 0.075 wt % DAROCURE® 1173 boaa, and 0.025 wt % IRGACURE® 651 was prepared, then cooled to 12° C. The resulting monomer mixture then was polymerized for 12.5 minutes under a UV light (UV intensity=20 mW/cm$^2$). The resulting PAA hydrogel was extruded through a KitchenAid Model K5SS mixer fitted with a meat grinder attachment. Then, varying amounts of ULTRA WHITE® 90 clay were added to the PAA hydrogel, followed by two extrusions. Nest, sodium carbonate was added to the clay-containing hydrogel to neutralize the acrylic acid groups 75 mol %, followed by two additional extrusions. The clay-containing PAA hydrogels were dried at 150° C. for one hour, then milled and sized to 150 to 800 µm. The dry particles then were surface crosslinked by spraying a solution containing 0.1 wt % EGDGE, 3.35 wt % water, and 1.65 wt % 1,2-propylene glycol, each based on particle weight, onto the particles and subsequent heating at 150° C. for one hour. The fluid absorbent properties of the resulting SAP-clay particles are summarized as follows:

| Amount of clay (in wt %) added to the unneutralized hydrogel (boaa) | CRC (g/g) Experimental | CRC (g/g) Theoretical | AUL 0.3 psi (1 hr) (g/g) Experimental | AUL 0.3 psi (1 hr) (g/g) Theoretical | AUL 0.7 psi (1 hr) (g/g) Experimental | AUL 0.7 psi (1 hr) (g/g) Theoretical | Free Swell Rate (g/g sec) |
|---|---|---|---|---|---|---|---|
| 0 | 29.7 | 29.7 | 30.5 | 30.5 | 24.3 | 24.3 | 0.32 |
| 5 | 27.9 | 28.2 | 27.9 | 29.0 | 24.1 | 23.0 | 0.36 |
| 10 | 26.9 | 26.8 | 27.5 | 27.5 | 23.6 | 21.8 | 0.39 |
| 15 | 26.7 | 25.3 | 28.1 | 25.9 | 23.3 | 20.6 | 0.43 |
| 20 | 27.1 | 23.8 | 27.0 | 24.4 | 22.9 | 19.4 | 0.46 |
| 25 | 25.7 | 22.3 | 26.3 | 22.9 | 20.6 | 18.2 | 0.48 |
| 30 | 24.8 | 20.8 | 25.2 | 21.4 | 20.9 | 17.0 | 0.51 |
| 35 | 24.9 | 19.3 | 25.1 | 19.8 | 19.8 | 15.8 | 0.52 |
| 40 | 24.3 | 17.8 | 24.3 | 18.3 | 18.5 | 14.3 | 0.50 |
| 45 | 23.3 | 16.4 | 24.6 | 16.8 | 18.5 | 13.3 | 0.53 |
| 50 | 23.5 | 14.9 | 23.7 | 15.2 | 18.2 | 12.1 | 0.54 |

The above table shows the theoretical and experimental values for absorbance under load (AUL) (0.3 psi), AUL (0.7 psi), and centrifuge retention capacity (CRC). The data shows that experimental AUL and CRC values for SAP-clay particles of the present invention are substantially greater than expected.

The above table illustrates the effect of adding a clay to an SAP hydrogel, prior to neutralization, on the absorbent properties of the SAP particles. In the test results set forth above, the absorbent SAP particles were tested for absorption under load at 0.3 psi and 0.7 psi (AUL (0.3 psi) and AUL (0.7 psi)) after one hour. Absorption under load (AUL) is a measure of the ability of an SAP to absorb fluid under an applied pressure. The AUL was determined by the following method.

An SAP (0.160 g+/−0.001 g) is carefully scattered onto a 140 micron, water-permeable mesh attached to the base of a hollow plexiglas cylinder with an internal diameter of 25 mm. The sample is covered with a 100 g cover plate and the cylinder assembly weighed. This gives an applied pressure of 20 g/cm$^2$ (0.3 psi). Alternatively, the sample can be covered with a 250 g cover plate to give an applied pressure of 51 g/cm$^2$ (0.7 psi). The screened base of the cylinder is placed in a 100 mm petri dish containing 25 milliliters of a test solution (usually 0.9% saline), and the polymer is allowed to absorb for 1 hour. By reweighing the cylinder assembly, the AUL (at a given pressure) is calculated by dividing the weight of liquid absorbed by the dry weight of polymer before liquid contact.

The CRC (centrifuge retention capacity) test is designed to measure the amount of saline solution retained inside an absorbent composition subjected to a specific centrifugal force. The measurement of CRC is disclosed in U.S. Pat. No. 6,187,828 and U.S. Pat. No. 5,633,316, each incorporated herein by reference.

The Free Swell Rate (FSR) of an SAP is determined by allowing the SAP particles to absorb saline without agitation or pressure. The time required to absorb the fluid is noted and reported in grams of fluid absorbed per gram of polymer per second. The following procedure was performed in triplicate at 23±2° C. and 50±10% relative humidity.

An SAP (1.00±0.01 g) is weighed directly into a tared 30 cm$^3$ beaker (32-34 mm by 50 mm height) to an accuracy of 0.0001 g. The exact weight of the SAP is recorded as $W_A$ grams. The SAP particles are distributed over the bottom of the beaker, gently tapping the beaker and shaking horizontally to avoid lumps. The test solution (0.9 wt % saline solution) (20±0.01 g) is weighed into a tared 50 cm$^3$ beaker, and the weight is recorded as $W_1$ to an accuracy of 0.01 g. The entire solution is carefully and quickly poured onto the SAP particles in the 30 cm$^3$ beaker and a timer is started immediately. The SAP particles are not moved or agitated during swelling. The time measurement is stopped when the last portion of the undisturbed fluid meets the swelling SAP particles. The end point is easier to observe by positioning the beaker on a Perspex platform to allow a full three-dimensional view of the test, and observing light refracted through the sample. This observation can be assisted by positioning a small lamp near the sample. The time is recorded at $t_s$ seconds. At $t_s$, a surface pool of fluid is no longer apparent from the reflected light, although some fluid is still slightly visible around the edges of the swollen SAP particles. The 50 cm$^3$ beaker is reweighed to an accuracy of 0.01 g, and the weight of the remaining fluid is recorded as $W_2$ grams. The Free Swell Rate for each test sample, and the average result for the three tests, are calculated. The difference between the highest and lowest replicate result should be less than 10% of the average value obtained.

Calculation:

Weight of saline solution absorbed by the polymer, $W_F$:
$W_F = W_1 - W_2$

The FSR is calculated as follows: $FSR = W_F/(t_s \times W_A)$

COMPARATIVE EXAMPLE 4

Example 3 was repeated, except the PAA hydrogels first were neutralized with sodium carbonate, followed by the addition of varying amounts of clay. The fluid absorbent properties of the comparative SAP-clay particles are summarized below:

| Amount of clay (in wt %) added to the unneutralized hydrogel (boaa) | CRC (g/g) Experimental | CRC (g/g) Theoretical | AUL 0.3 psi (1 hr) (g/g) Experimental | AUL 0.3 psi (1 hr) (g/g) Theoretical | AUL 0.7 psi (1 hr) (g/g) Experimental | AUL 0.7 psi (1 hr) (g/g) Theoretical | Free Swell Rate (g/g sec) |
|---|---|---|---|---|---|---|---|
| 0 | 30.1 | 29.7 | 30.3 | 30.5 | 24.1 | 24.3 | 0.29 |
| 5 | 28.1 | 28.2 | 27.4 | 29.0 | 22.8 | 23.0 | 0.27 |
| 10 | 26.9 | 26.8 | 27.0 | 27.5 | 22.1 | 21.8 | 0.31 |
| 15 | 25.9 | 25.3 | 26.3 | 25.9 | 21.0 | 20.6 | 0.30 |
| 20 | 25.2 | 23.8 | 25.4 | 24.4 | 19.2 | 19.4 | 0.32 |
| 25 | 24.8 | 22.3 | 23.5 | 22.9 | 18.4 | 18.2 | 0.33 |
| 30 | 23.5 | 20.8 | 22.7 | 21.4 | 17.3 | 17.0 | 0.31 |
| 35 | 23.0 | 19.3 | 20.4 | 19.8 | 15.5 | 15.8 | 0.34 |
| 40 | 22.2 | 17.8 | 20.1 | 18.3 | 14.6 | 14.3 | 0.35 |
| 45 | 22.4 | 16.4 | 18.9 | 16.8 | 14.0 | 13.3 | 0.32 |
| 50 | 20.9 | 14.9 | 17.5 | 15.3 | 13.5 | 12.1 | 0.33 |

Example 7 and Comparative Example 4 further illustrate the advantages of neutralizing an SAP hydrogel after addition of a clay to the hydrogel, e.g., improved FSR and AUL, especially at higher amounts of clay in the SAP particles.

EXAMPLE 8

A 10 L capacity polyethylene vessel, well insulated by foamed polymer material, was charged with 3400 g demineralized water and 1400 9 acrylic acid. N,N'-methylenbisacrylamide (2.8 g) then was added as copolymerization crosslinker. At a temperature of 10° C., (2.2 g) 2,2'-azobisamidinopropane dihydrochloride dissolved in 25 g demineralized water, and potassium peroxodisulfate (4 g) dissolved in 150 g demineralized water, were added to the reaction mixture, in succession, with stirring. The resulting solution then was deoxygenated by bubbling a nitrogen stream through the solution for 30 minutes, followed by the addition of ascorbic acid (0.4 g) dissolved in 25 g demineralized water. The reaction solution then was allowed to stand without stirring, and the temperature of the polymerization rose for about 96° C. A solid PAA hydrogel was obtained, and the subsequently was comminuted mechanically. Varying amounts of a clay slurry (ULTRA WHITE® 90 containing 70 wt % clay) were added to the hydrogel, followed by two extrusions. Next, a sodium hydroxide solution (50% by weight) was added to the clay-containing hydrogel to neutralize the acrylic acid groups 74 mol %, followed by two additional extrusions. The hydrogel then was dried, ground, and classified to a particle size distribution of 106 to 850 μm. Dried SAP particles (1 kg) then were sprayed in a plowshare mixer with a solution containing demineralized water (40 g), methanol (40 g), and EGDGE (1.2 g), followed by heating at 140° C. for 2 hours.

The SAP-clay particles were tested for acquisition time/rewet under pressure:

recorded as Acquisition Time 1. Thereafter, the pad is weighed with a plate for 20 minutes, the load being further maintained at 13.6 g/cm². Thereafter, the plate is removed, and filter paper (Schleicher & Schuell, 1450 CV) (10 g±0.5 g) is placed on the central spot and loaded with a weight (area 10 cm×10 cm, weight 3.5 kg) for 15 seconds. The weight then is removed and the filter paper is reweighed. The weight difference is noted as Rewet 1. Thereafter, the plastic plate with application ring again is placed on the pad and the liquid is applied a second time. The measured time is noted as Acquisition Time 2. The procedure is repeated as described, but 45 g±0.5 g of filter paper is used for the Rewet test. Rewet 2 is measured. The same method is employed to determine Acquisition Time 3. Rewet 3 is determined using 50 g±0.5 g filter paper.

COMPARATIVE EXAMPLE 5

A 10 L capacity polyethylene vessel, well insulated by foamed polymer material, was charged with 3400 g demineralized water and 1400 g acrylic acid. N,N'-methylenbisacrylamide (2.8 g) then was added as copolymerization crosslinker. At a temperature of 10° C., of 2,2'-azobisamidinopropane dihydrochloride (2.2 g) dissolved in 25 g of demineralized water, and potassium peroxodisulfate (4 g)

| Amount of clay (in wt %) added to the unneutralized hydrogel (boaa) | Acquisition Time 1 (seconds) | Acquisition Time 2 (seconds) | Acquisition Time 3 (seconds) | Rewet 1 (grams) | Rewet 2 (grams) | Rewet 3 (grams) |
| --- | --- | --- | --- | --- | --- | --- |
| 0 | 30 | 95 | 152 | <0.1 | 0.6 | 2.8 |
| 5 | 29 | 80 | 131 | <0.1 | 0.6 | 2.6 |
| 10 | 27 | 75 | 116 | <0.1 | 0.5 | 2.4 |
| 15 | 25 | 73 | 94 | <0.1 | 0.5 | 2.9 |
| 20 | 23 | 68 | 82 | <0.1 | 0.7 | 3.2 |
| 25 | 20 | 62 | 74 | <0.1 | 0.8 | 3.8 |
| 30 | 17 | 55 | 69 | <0.1 | 0.8 | 4.2 |

The acquisition time and rewet values were determined as follows:

The acquisition time/rewet under pressure test is performed using laboratory pads. To produce these laboratory pads, 11.2 g of cellulose fluff and 13.0 g of SAP particles are homogeneously fluidized in an air box and by application of a slight vacuum laid down on a mold 12 by 26 cm in size. This composition then is wrapped in tissue paper and compressed twice for 15 seconds under a pressure of 200 bar. A resulting laboratory pad is attached to a horizontal surface. The center of the pad is determined and marked. Saline solution (0.9 wt % of NaCl) is applied through a plastic plate having a ring in the middle (internal diameter of ring: 6.0 cm, height: 4.0 cm). The plastic plate is loaded with additional weights such that the total load on the pad is 13.6 g/cm². The plastic plate is placed on the pad such that the center of the pad also is the center of the application ring. Saline solutions (80 ml) are applied three times. The saline solution is measured in a measuring cylinder and applied as a single dose to the pad through the ring in the plate. Simultaneously, time is measured until the solution has completely penetrated into the pad. The measured time is dissolved in 150 g of demineralized water, were added to the reaction mixture in succession with stirring. The resulting solution was deoxygenated by bubbling a nitrogen stream through the solution for 30 minutes, followed by the addition of ascorbic acid (0.4 g) dissolved in 25 g of demineralized water. The reaction solution then was allowed to stand without stirring, and the temperature of the polymerization rose to about 96° C. A solid PAA hydrogel was obtained, and the hydrogel was subsequently mechanically comminuted. Varying amounts of a ULTRA WHITE® 90 clay slurry were added to the PAA hydrogel, followed by two extrusions. Next, a sodium hydroxide solution (50% by weight) was added to the clay-containing hydrogel to neutralize the acrylic acid groups to 74 mol %, followed by two additional extrusions. The PAA-clay hydrogel then was dried, ground, and classified to a particle size distribution of 106 to 850 μm. The SAP-clay particles (1 kg) then were sprayed in a plowshare mixer with a solution containing 40 g demineralized water, 40 g methanol, and 1.2 g EGDGE, followed by heating at 140° C. for 2 hours.

The resulting SAP-clay particles were tested for acquisition time/rewet under pressure by the above procedure.

| Amount of clay (in wt %) added to the unneutralized hydrogel (boaa) | Acquisition Time 1 (seconds) | Acquisition Time 2 (seconds) | Acquisition Time 3 (seconds) | Rewet 1 (grams) | Rewet 2 (grams) | Rewet 3 (grams) |
| --- | --- | --- | --- | --- | --- | --- |
| 0 | 32 | 89 | 148 | <0.1 | 0.7 | 2.9 |
| 5 | 30 | 88 | 142 | <0.1 | 0.7 | 3.2 |
| 10 | 31 | 92 | 147 | <0.1 | 0.8 | 3.5 |
| 15 | 34 | 97 | 159 | 0.1 | 1.2 | 4.3 |
| 20 | 36 | 105 | 174 | 0.2 | 1.5 | 4.9 |
| 25 | 37 | 110 | 192 | 0.2 | 1.8 | 6.9 |
| 30 | 40 | 117 | 215 | 0.3 | 2.1 | 9.8 |

The above comparative table shows a substantial increase in acquisition time and increased rewet values. Example 8 and Comparative Example 5, therefore, further illustrate the advantages of neutralizing an SAP hydrogel after addition of a clay to the hydrogel.

The above test results show that the absorbent SAP-clay particles of the present invention can be used to absorb aqueous fluids. The fluid can be a body fluid, an industrial waste, or any other fluid that one desires to absorb. The absorbed fluid can be any water-containing fluid, and typically contains electrolytes, for example, urine, blood, saline, menses, and similar liquids.

The SAP-clay particles are especially useful in absorbent articles, such as diapers, adult incontinence products, tampons, and sanitary napkins. The present SAP-clay particles, therefore, are useful in personal hygiene articles comprising:
 (A) a fluid-pervious topsheet;
 (B) a fluid-impervious backsheet;
 (C) a core positioned between (A) and (B), said core comprising:
  (C1) about 10 to 100% by weight of the SAP-clay particles of the present invention, and
  (C2) 0 to about 90% by weight of a fiber material;
 (D) optionally one or more tissue layers positioned directly above and/or below said core (C); and
 (E) optionally an acquisition layer positioned between (A) and (C).

The fluid-pervious topsheet (A) is the layer which is in direct contact with the skin of the wearer. Topsheet (A) generally comprises synthetic or cellulosic fibers or films, i.e., polyesters, polyolefins, rayon, or natural fibers, such as cotton. In the case of nonwoven materials, the fibers generally are joined together by binders such as a polyacrylate. Preferred materials are polyesters, rayon and blends thereof, polyethylene, and polypropylene. The fluid-impervious layer (B) is generally a sheet of polyethylene or polypropylene.

The core (C) includes SAP-clay particles (C1) of the present invention, and also can include a fiber material (C2). Fiber material (C2) typically is hydrophilic, i.e., aqueous fluids are rapidly distributed across the fibers. The fiber material typically is cellulose, modified cellulose, rayon, or a polyester, such as polyethylene terephthalate. Preferred fibers are cellulose fibers, such as pulp. The fibers generally have a diameter of about 1 to about 200 µm, preferably about 10 to about 100 µm, and a minimum length of about 1 mm.

The amount of fiber material (C2) based on the total weight of the core is typically about 20% to about 80% by weight, preferably about 40% to about 70% by total weight of C(1) and C(2). Core (C) typically also can be a heavily loaded core (e.g., 60-95 wt % SAP-clay particles/5-40 wt % fluff).

The SAP-clay particles often are present in core (C) as a pressed sheet containing the particles, and optionally fluff and/or nonwoven fibers. A single absorbent layer or sheet containing SAP-clay particles of the present invention can be used as the absorbent component of a core (C). Preferably, a plurality of absorbent layers or sheets are used in the core (C), more preferably together with a wicking layer (e.g., a tissue layer) between absorbent layers or sheets to provide improved wicking of a fluid between and through the absorbent sheets. In more preferred embodiments, at least one of the absorbent layers or sheets in a core (C) contains nonwoven fibers to improve wet strength of the absorbent core and assist in wicking.

A preferred core (C) contains two to five absorbent layers or sheets. By utilizing a laminate of thin absorbent layers or sheets, as opposed to a single, thicker absorbent layer or sheet, horizontal expansion of the core is decreased, and vertical expansion is promoted. This feature provides a good fluid transport through the core, provides a better fitting diaper after an initial insult, and avoids leaking when the diaper is subsequently rewet by a second and additional insult. In more preferred embodiments, core (C) contains a laminate of two or more absorbent layers or sheets of SAP-clay particles wherein a wicking layer is positioned between each absorbent sheet layer or sheet, and on top and at the bottom of the laminate.

An absorbent layer or sheet containing SAP-clay particles of the present invention, or a laminate comprising such layers or sheets, is present in an absorbent core to provide a desired basis weight (i.e., weight of SAP in the core) of about 50 to about 800 gsm (grams/square meter), and preferably about 150 to about 600 gsm. To achieve the full advantage of the present invention, the basis weight is about 300 to about 550 gsm. The desired basis weight of the core is related to the end use of the core. For example, diapers for newborns have a low basis weight, as opposed to a medium basis weight for toddlers, and a high basis weight for overnight diapers.

In a preferred embodiment, a present diaper core consists essentially of a topsheet (A), a core (C), and a backsheet (B), i.e., an acquisition layer is not present. An example of a topsheet (A) is staple length polypropylene fibers having a denier of about 1.5, such as Hercules-type 151 polypropylene marketed by Hercules, Inc., Wilmington, Del. As used herein, the term "staple length fibers" refers having a length of at least about 15.9 mm (0.62 inches). The backsheet (B) is impervious to liquids, and typically is manufactured from a thin plastic film, although other flexible liquid impervious materials also can be used. The backsheet prevents exudates absorbed and contained in the absorbent core (C) from wetting articles, such as bed sheets and undergarments, that contact the diaper.

For an absorbent article having a core (C) containing a "fluff" component, the "fluff" comprises a fibrous material in the form of a web or matrix. Fibers include naturally occurring fibers (modified or unmodified). Examples of suitable unmodified/modified naturally occurring fibers include cotton, Esparto grass, bagasse, kemp, flax, silk, wool, wood pulp, chemically modified wood pulp, and jute. See WO 98/37149 and U.S. Pat. No. 5,859,074, each incorporated herein by reference, for a complete discussion of "fluff" components for use in an absorbent sheet article.

The cores also can include an optional nonwoven fiber, for example, polypropylene, polyethylene, polyethylene terephthalate, viscose, and mixtures thereof. Also, an open fiber mesh of nonwoven fibers can be used, for example, cellulose acetate fiber. Nonwoven fibers can be made by drylaid thermobonded, carded air-through bonded, spunbond, or spun-meltblown-spun processes. Nonwoven fibers impart additional wet strength to an absorbent layer or sheet when used in an amount of about 10 to about 20 grams per square meter (gsm) of sheet material.

Suitable fibers, and fiber meshes, can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides (e.g., nylon), polyesters (e.g., DACRON® or KODEL®), polyurethanes, polystyrenes, and the like.

Hydrophilic fibers are preferred, and include rayon, polyester fibers, such as polyethylene terephthalate (e.g., DACRON®), hydrophilic nylon (e.g., HYDROFIL®), and the like. Suitable hydrophilic fibers can also be obtained by hydrophilizing hydrophobic fibers, such as surfactant-treated or silica-treated thermoplastic fibers derived from, for example, polyolefins, such as polyethylene or polypropylene, polyacrylics, polyamides, polystyrenes, polyurethanes, and the like.

The improved results demonstrated by a core containing SAP-clay particles of the present invention permit the thickness of the core to be reduced. Typically, cores contain 50% or more fluff or pulp to achieve rapid liquid absorption while avoiding problems like gel blocking. The present cores, which contain SAP-clay particles acquire liquids sufficiently fast to avoid problems, like gel blocking, and, therefore, the amount of fluff or pulp in the core can be reduced, or eliminated. A reduction in the amount of the low-density fluff results in a thinner core, and, accordingly, a thinner diaper. Therefore, a core of the present invention can contain at least 50% SAP-clay particles, preferably at least 60%, and up to 80% of the SAP-clay particles. In various embodiments, the presence of a fluff is no longer necessary, or desired.

Many modifications and variations of the invention as hereinbefore set forth can be made without department from the spirit and scope thereof, and, therefore, only such limitations should be imposed as are indicated by the appended claims.

What is claimed is:

1. Superabsorbent particles comprising:
   (i) about 50% to about 95%, by weight, of a superabsorbent polymer; and
   (ii) about 5% to about 50%, by weight, of a clay, said particles prepared by a method comprising the steps of:
   (a) polymerizing an unneutralized monomer capable of providing a superabsorbent absorbent polymer in the presence of an internal crosslinking monomer to form a superabsorbent polymer hydrogel;
   (b) comminuting the superabsorbent polymer hydrogel to form superabsorbent polymer hydrogel particles;
   (c) admixing a clay with the superabsorbent polymer hydrogel particles to form superabsorbent polymer-clay hydrogel particles;
   (d) then neutralizing the superabsorbent polymer-clay hydrogel particles by adding a sufficient amount of a neutralizing agent to neutralize the hydrogel particles 50% to 100%, by weight; and
   (e) drying the neutralized superabsorbent polymer-clay hydrogel particles of step (d) to provide the superabsorbent particles.

2. The particles of claim 1 wherein the method further comprises:
   (f) surface crosslinking the superabsorbent particles of step (e).

3. The particles of claim 1 wherein the superabsorbent polymer is present in an amount of about 60% to about 90%, by weight, and the clay is present in an amount of about 10% to about 40%, by weight.

4. The particles of claim 1 wherein the superabsorbent polymer comprises a polymerized α,β-unsaturated carboxylic acid, or a salt or an anhydride thereof.

5. The particles of claim 1 wherein the unneutralized monomer is selected from the group consisting of acrylic acid, methacrylic acid, ethacrylic acid, α-chloroacrylic acid, α-cyanoacrylic acid, β-methylacrylic acid, α-phenylacrylic acid, β-acryloxypropionic acid, sorbic acid, α-chlorosorbic acid, angelic acid, cinnamic acid, p-chlorocinnamic acid, β-stearylacrylic acid itaconic acid, citraconic acid, mesaconic acid, glutaconic acid, aconitic acid, maleic acid, fumaric acid, tricarboxyethylene, maleic anhydride, vinyl sulfonic acid, allyl sulfonic acid, vinyl toluene sulfonic acid, styrene sulfonic acid, sulfoethyl acrylate, sulfoethyl methacrylate, sulfopropyl acrylate, sulfopropyl methacrylate, sulfopropyl acrylate, sulfopropyl methacrylate, 2-hydroxy-3-methacryloxypropyl sulfonic acid, 2-acrylamide-2-methylpropane sulfonic acid, methacryloxy ethyl phosphate, and mixtures thereof.

6. The particles of claim 1 wherein the superabsorbent polymer is selected from the group consisting of poly(acrylic acid), a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylphosphonic acid), a poly(vinylphosphoric acid), a poly(vinylsulfuric acid), a sulfonated polystyrene, salts thereof, and mixtures thereof.

7. The particles of claim 1 wherein the superabsorbent polymer is selected from the group consisting of a poly(vinylamine), a poly(dialkylaminoalkyl(meth)acrylamide), a polyethylenimine, a poly(allylamine), a poly(allylguanidine), a poly(dimethyldiallylammonium hydroxide), a quaternized polystyrene derivative, a guanidine-modified polystyrene, a quaternized poly((meth)acrylamide) or ester analog, a poly(vinylguanidine), salts thereof, and mixtures thereof.

8. The particles of claim 1 wherein the superabsorbent polymer comprises polyacrylic acid neutralized about 25% to 100%.

9. The particles of claim 1 wherein the clay is a swelling clay selected from the group consisting of montmorillonite, saponite, nontronite, laponite, beidelite, hectorite, sauconite, stevensite, vermiculite, volkonskoite, magadite, medmontite, kenyaite, and mixtures thereof.

10. The particles of claim 1 wherein the clay is a non-swelling clay selected from the group consisting of a kaolin mineral, a serpentine mineral, a mica mineral, a chlorite mineral, sepolite, palygorskite, bauxite, and mixtures thereof.

11. The particles of claim 10 wherein the nonswelling clay comprises a kaolinite.

12. The particles of claim 1 wherein the clay is an organophilic clay having an organic component and an inorganic component.

13. The particles of claim 12 wherein the inorganic component of the organophilic clay comprises smectite, bentonite, hectorite, montmorillonite, beidelite, saponite, stevensite, nontronite, illite, attapulgite, a zeolite, fuller's earth, and mixtures thereof.

14. The particles of claim 12 wherein the inorganic component of the organophilic clay comprises montmorillonite.

15. The particles of claim 12 wherein the organic component of the organophilic clay comprises

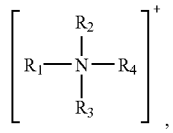

wherein $R_1$ is an alkyl group having at least 20 carbon atoms, $R_2$ is hydrogen, benzyl, or an alkyl group having at least 10 carbon atoms, and $R_3$ and $R_4$, independently, are a lower alkyl group;

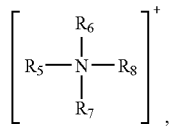

wherein $R_5$ is $CH_3$ or $C_6H_5CH_2$, $R_6$ is $C_6H_5CH_2$, and $R_7$ and $R_8$, independently, are alkyl groups containing long chain alkyl radicals having 14 to 22 carbon atoms; or a mixture thereof.

16. The particles of claim 12 wherein the organophilic clay is selected from the group consisting of dimethyl benzyl (hydrogenated tallow) ammonium bentonite, methyl benzyl di(hydrogenated tallow) ammonium bentonite, dimethyl di(hydrogenated tallow) ammonium bentonite, methyl bis (2-hydroxyethyl) octadecyl ammonium bentonite, a bentonite clay treated with an amine containing three to eight carbon atoms, and mixtures thereof.

17. A method of absorbing an aqueous medium comprising contacting the medium with the superabsorbent particles of claim 1.

18. The method of claim 17 wherein the aqueous medium contains electrolytes.

19. The method of claim 18 wherein the electrolyte-containing aqueous medium is selected from the group consisting of urine, saline, menses, and blood.

20. An absorbent article comprising the superabsorbent particles of claim 1.

21. The article of claim 20 wherein the article is a diaper or a catamenial device.

22. A diaper having a core, said core comprising at least 10% by weight of the superabsorbent particles of claim 1.

23. The diaper of claim 22 wherein the core comprises 20-80% by weight of the superabsorbent particles.

24. The diaper of claim 22 further comprising a topsheet in contact with a first surface of the core, and a backsheet in contact with a second surface of the core, said second core surface opposite from said first core surface.

25. The diaper of claim 24 further comprising an acquisition layer disposed between the topsheet and the core.

26. A method of manufacturing superabsorbent polymer-clay particles comprising the steps of:
   (a) forming an aqueous monomer mixture comprising (i) at least one monomer, in an unneutralized form, capable of forming a superabsorbent polymer, (ii) an internal crosslinking monomer, and (iii) a polymerization catalyst;
   (b) polymerizing the monomer in the aqueous mixture to form a superabsorbent polymer hydrogel;
   (c) comminuting the superabsorbent polymer hydrogel to provide superabsorbent polymer hydrogel particles;
   (d) admixing a clay with the superabsorbent polymer hydrogel particles to form superabsorbent-clay hydrogel particles;
   (e) neutralizing the superabsorbent polymer-clay hydrogel particles by adding a base to the superabsorbent polymer-clay hydrogel particles; and
   (f) drying the neutralized superabsorbent polymer-clay hydrogel particles for a sufficient time at a sufficient temperature to provide dry superabsorbent polymer-clay particles.

27. The method of claim 26 wherein the monomer capable of forming the superabsorbent polymer is selected from the group consisting of acrylic acid, methacrylic acid, ethacrylic acid, α-chloroacrylic acid, α-cyanoacrylic acid, β-methylacrylic acid, α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, maleic anhydride, vinyl sulfonic acid, allyl sulfonic acid, vinyl toluene sulfonic acid, styrene sulfonic acid, sulfoethyl acrylate, sulfoethyl methacrylate, sulfopropyl acrylate, sulfopropyl methacrylate, sulfopropyl acrylate, sulfopropyl methacrylate, 2-hydroxy-3-methacryloxypropyl sulfonic acid, 2-acrylamide-2-methylpropane sulfonic acid, methacryloxy ethyl phosphate, and mixtures thereof.

28. The method of claim 26 wherein the superabsorbent polymer is selected from the group consisting of poly (acrylic acid), a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, poly(vinylsulfonic acid), poly(vinylphosphonic acid), poly(vinylphosphoric acid), poly(vinylsulfuric acid), sulfonated polystyrene, a poly(vinylamine), a poly(dialkylaminoalkyl(meth)acrylamide), a lightly crosslinked polyethylenimine, a poly(allylamine), a poly(allylguanidine), a poly(dimethyldiallylammonium hydroxide), a quaternized polystyrene derivative, a guanidine-modified polystyrene, a quaternized poly((meth)acrylamide) or ester analog, a poly(vinylguanadine), and mixtures thereof.

29. The method of claim 26 wherein the neutralized superabsorbent polymer-clay hydrogel particles in step (e) have a degree of neutralization of about 50 to about 80.

* * * * *